(12) United States Patent
Wang

(10) Patent No.: US 10,301,258 B2
(45) Date of Patent: May 28, 2019

(54) BENZENE SULFONAMIDE DERIVATIVES AS HIV INTEGRASE INHIBITORS

(71) Applicant: HOWARD UNIVERSITY, Washington, DC (US)

(72) Inventor: Xiang Simon Wang, Washington, DC (US)

(73) Assignee: HOWARD UNIVERSITY, Washington, DC (US)

(*) Notice: Subject to any disclaimer, the term of this patent is extended or adjusted under 35 U.S.C. 154(b) by 0 days.

(21) Appl. No.: 15/114,289

(22) PCT Filed: Feb. 26, 2015

(86) PCT No.: PCT/US2015/017781
§ 371 (c)(1),
(2) Date: Jul. 26, 2016

(87) PCT Pub. No.: WO2015/130947
PCT Pub. Date: Sep. 3, 2015

(65) Prior Publication Data
US 2017/0008839 A1   Jan. 12, 2017

Related U.S. Application Data

(60) Provisional application No. 61/944,990, filed on Feb. 26, 2014.

(51) Int. Cl.
*C07C 311/41* (2006.01)
*A61K 31/18* (2006.01)
*C07C 311/18* (2006.01)

(52) U.S. Cl.
CPC ............ *C07C 311/41* (2013.01); *A61K 31/18* (2013.01); *C07C 311/18* (2013.01)

(58) Field of Classification Search
CPC ...... C07C 311/41; C07C 311/18; A61K 31/18
See application file for complete search history.

(56) References Cited

U.S. PATENT DOCUMENTS

| 2002/0072512 A1 | 6/2002 | Salvemini |
| 2007/0259823 A1 | 11/2007 | Nair et al. |

(Continued)

FOREIGN PATENT DOCUMENTS

WO   2007/065032 A2   6/2007

OTHER PUBLICATIONS

Smith et al (Rapid Screening of HIV Reverse Transcriptase and Integrase Inhibitors. J. Vis. Exp. (86), e51400) (Year: 2014).*

(Continued)

*Primary Examiner* — Angela C Brown-Pettigrew
(74) *Attorney, Agent, or Firm* — Fitch, Even, Tabin & Flannery LLP

(57) ABSTRACT

Methods for treating retroviral infection or inhibiting HIV integrase in target cells or in a patient involve administering to target cells or to a patient in need of treatment an effective amount of at least one having a disulfonamide scaffold which is represented by the formula:

(1)

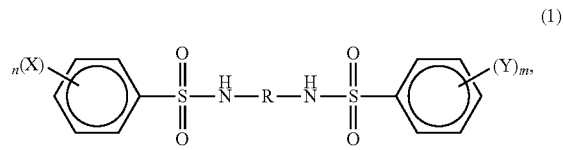

wherein, independent of each other,
each X independently represents hydrocarbyl, halogeno, amino, substituted amino, or alkoxy, wherein substi-
(Continued)

tuted amino is represented by —NR$_3$,R$_4$ wherein R$_3$ and R$_4$, are not both hydrogen and independently represent alkyl or alkenyl, n is an integer of 0, 1, 2, or 3, each Y independently represents hydrocarbyl, halogeno, amino, substituted amino or alkoxy, wherein substituted amino is represented by —NR$_3$,R$_4$ wherein R$_3$ and R$_4$, are not both hydrogen and independently represent alkyl or alkenyl, m is an integer of 0, 1, 2, or 3, and R represents di-valent hydrocarbyl, substituted or unsubstituted.

20 Claims, 2 Drawing Sheets

(56) References Cited

U.S. PATENT DOCUMENTS

| | | |
|---|---|---|
| 2010/0137194 A1 | 6/2010 | Lawrence et al. |
| 2011/0178108 A1 | 7/2011 | Jiang et al. |
| 2011/0280940 A1 | 11/2011 | Kiss et al. |
| 2012/0022054 A1 | 1/2012 | Bernarous et al. |
| 2013/0123266 A1 | 5/2013 | Zagury et al. |

OTHER PUBLICATIONS

International Search Report for PCT/PCT/US15/17781 dated May 29, 2015 (2 Pages).

* cited by examiner

BENZENDE SULFONAMIDE DERIVATIVES AS HIV INTEGRASE INHIBITORS

CROSS-REFERENCE TO RELATED APPLICATIONS

This application is a U.S. national phase application filed under 35 U.S.C. § 371 of International Application No. PCT/US2015/017781, filed Feb. 26, 2015, designating the United States, and claims priority from U.S. Provisional Application No. 61/944,990, filed Feb. 26, 2014, the complete disclosures of which applications are hereby incorporated herein by reference in their entirety for all purposes.

GOVERNMENT INTEREST

No government support was granted for this work.

FIELD OF INVENTION

This work has identified novel compounds with antiviral activity, specifically novel integrase inhibitors for the treatment of HIV. By inhibiting nuclear import of HIV integrase with small molecule inhibitors, integration of HIV viral genomic DNA into host DNA has been prevented thereby blocking HIV replication.

BACKGROUND

The human immunodeficiency virus (HIV), as its name suggest, is characterized by progressive immunologic deterioration which over a period of time results in neurologic disorders and opportunistic infections leading to acquired immunodeficiency syndrome (AIDS). The search to find antiretroviral therapy for treatment of the 34 million people globally infected with Human Immunodeficiency Virus (HIV) is an ongoing one. Although there are over 20 antiretroviral drugs approved for the treatment of HIV that will halt replication of the virus, the complete eradication of this fatal disease remains a scientific challenge. Drug resistance, tolerability and HIV latency are major factors contributing to ART failure and ultimately success in finding a cure.[2-4] Hence, there remains a critical and unmet need to identify novel antiretroviral drug candidates active against HIV-1 resistant mutations for treatment of HIV-1 infection.

Integrase is one of the essential enzymes required for replication of HIV and is encoded by viral pol gene. Integration of virally transcribed cDNA into host DNA is an essential step for viral replication and the continuation of HIV life cycle. Upon synthesis of viral DNA in the cytoplasm of the cell, a series of interactions of viral proteins, matrix protein, a triple stranded cDNA flap and cellular cofactors, with integrase (IN) forms the pre-integration complex (PIC). Transport of viral DNA to the nucleus of the cell requires the formation of PIC which binds nuclear transport receptors via a nuclear localization signal (NLS) thereby allowing for entry into the nucleus where viral cDNA will integrate into host DNA. Successful integration of viral cDNA into host DNA is an essential step for viral replication and the continuation of HIV life cycle hence, IN is considered a good drug target for the development of ARV drugs.

There are multiple classes of antiretroviral (ARV) drugs that target various stages of the HIV life cycle which elicit unique mechanisms of action. As the mechanism of action of integrase (IN) and the evolution of IN resistant mutations is swiftly unfolding, IN represents an untapped source of undiscovered ARV drugs. The success rate for discovery and development of integrase inhibitors is quite low with only two IN inhibitors currently on the market, Raltegravir (RAL) developed by Merck & Co and Elvitegravir (EVG), as a combination therapy, developed by Gilead Science. Both drugs binds the catalytic site of IN located in the catalytic core domain and function by inhibiting the strand transfer process of vDNA into host DNA hence are referred to as integrase strand transfer inhibitors (INSTI). However due to the increasing clinical reports of INSTI resistance there is a need to design new class of IN inhibitors with novel mechanism of action. Specifically RAL and EVG exhibit consistant resistant pathways Q148HRQ/G140S and N155H/E92Q. A more recent approach to targeting IN is with small molecule inhibitors of LEDGF/p75 known as LEDGINs. Integrase inhibitors have been classified into five categories: (1) DNA-binding inhibitors, (2) 3' processing inhibitors, (3) nuclear translocation/import inhibitors, (4) strand transfer inhibitors, and (5) gap repair inhibitors. Currently there are no reports of small molecule inhibitors that target allosteric site on CTD of IN.

The structure of IN plays a major role in dictating its function hence, complete elucidation of its structure will contribute significantly to the discovery of integrase inhibitors. To date the complete crystal structure of IN has not been elucidated, however we do know IN comprises 288 amino and has three domains, N-terminal domain (NTD), catalytic core domain (CCD) and the C-terminal domain (CTD). Each IN monomer will combine to form a tetrameric IN structure. The NTD and CCD have conserved and functional motifs, while the CTD is the least conserved of the three. The conserved region of the NTD (residues 1-50) contains a sequence of HHCC residues that form a zinc finger motif which functions to chelate one zinc atom per IN monomer. In the absence of zinc the NTD of IN is destabilized and become disordered and formation of the multimeric form of IN is not achieved and could disrupt its activity.[22] The CCD (residues 51-212) conserved region comprises a triad of acidic residue that form the DDE motif It is essential for 3' processing and strand transfer processes. Integrase has nuclease activity that is site specific for cleaving two nucleosides at the 3' end of viral DNA, a process known as 3' processing. Subsequently, the strand transfer process ensues and it involves the 3 ends of viral DNA inserting into host DNA. The CTD (residues 213-288) on the other hand, is less conserved and is essential for IN-IN and non-specific IN-DNA (residues 220-270) interactions.

SUMMARY

Methods for treating against HIV-1 and for inhibiting HIV integrase in target cells or in a patient in need of treatment include administering certain anti-viral compounds having a disulfonamide scaffold for retroviral therapy including but not limited to treating HIV-1 are described.

The present invention demonstrates specificity of the molecules to bind to and inhibit HIV integrase activity as well as their antiviral activity against HIV-1, such as the HIV-1 lentiviral vector. Hence these compounds include anti-retrovirals that exhibit a novel mechanism of action against the HIV-1 virus and HIV integrase (IN).

A class of small molecules is identified as HIV integrase (IN) inhibitors that bind to site(s) targeting IN residue(s) so as to effectively inhibit HIV replication. Small molecules according to any of the formulas herein can bind to inhibit such residue(s), such as allosteric sites for residues K236/

K240 and R262/R263/K266, includes an exemplary such compound as described herein, such as compound 535.

DETAILED DESCRIPTION

Figure 1:
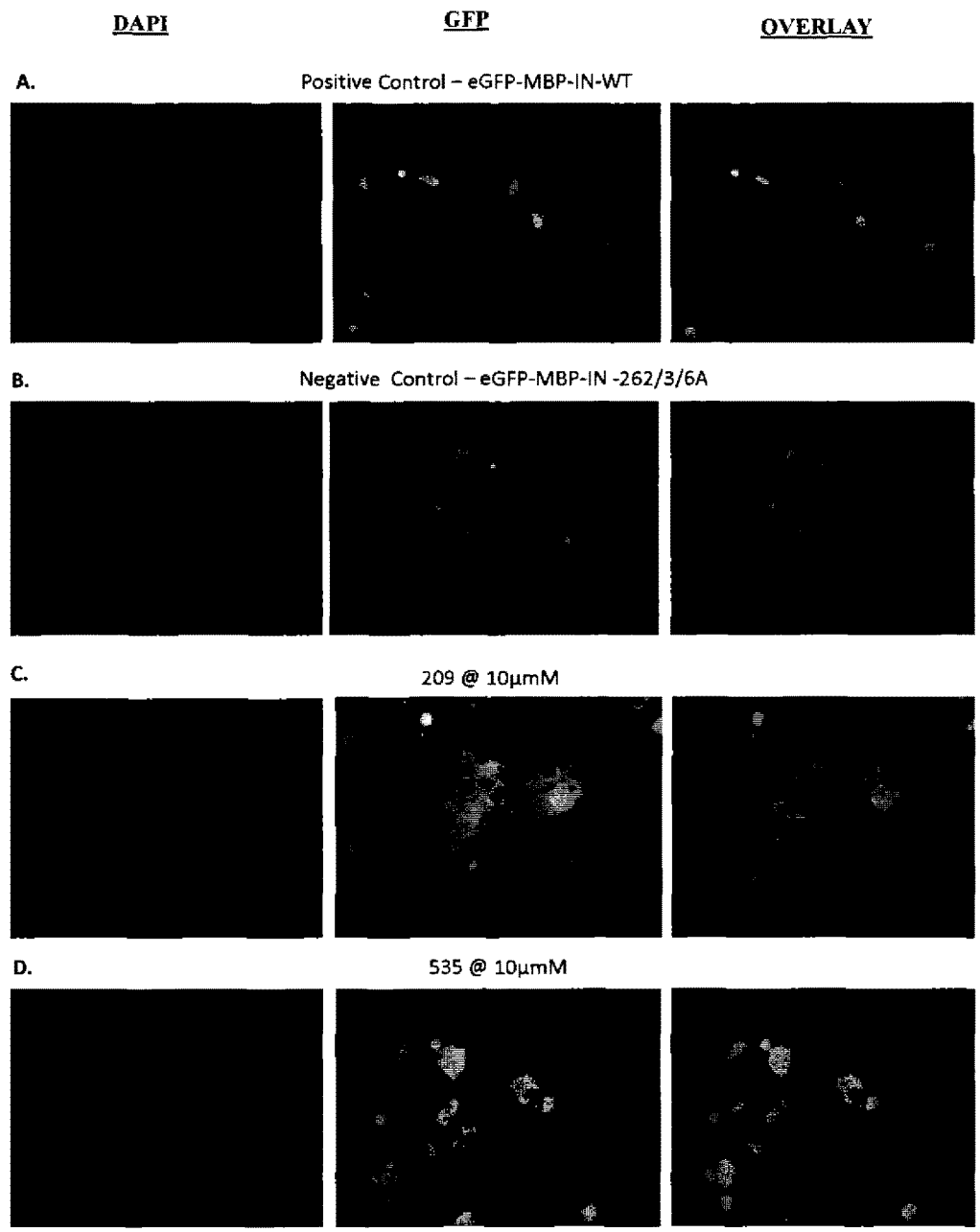
FIG. 1 shows screening assay results for C-terminal domain of HIV-1 IN, nuclear import inhibition.

A method for treating retroviral infections and more specifically inhibition of HIV infection comprises administering to an infected cell(s) or a patient in need of treatment an effective amount of at least one anti-viral compound, wherein the anti-viral compound comprises a compound having disulfonamide scaffold represented by the following general formula:

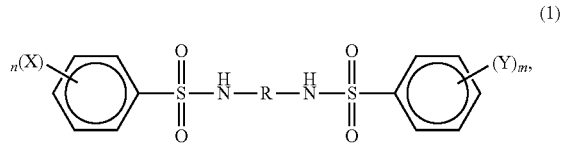

(1)

wherein, independent of each other,
X represents hydrocarbyl, halogeno, amino, substituted amino ($-NR_3,R_4$), and alkoxy,
n is an integer of 0, 1, 2, 3 or 4,
Y represents hydrocarbyl, halogeno, amino, substituted amino ($-NR_3,R_4$), and alkoxy;
m is an integer of 0, 1, 2, 3, or 4, and
R represents a di-valent hydrocarbyl, substituted or unsubstituted, such as di-valent aryl or divalent alkyl as examples. Independent of each other includes as to each X and to each Y, and to n and m.

In another of its aspects, a method for treating retroviral infections and more specifically inhibition of HIV infection comprises administering to an infected cell(s) or a patient in need of treatment an effective amount of at least one anti-viral compound, wherein the anti-viral compound comprises a compound having disulfonamide scaffold represented by the following formula (2):

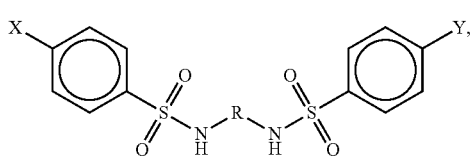

(2)

wherein, independent of each other,
X, Y and R are as stated above for formula (1).

In another of its aspects, a method for treating retroviral infections and more specifically inhibition of HIV infection comprises administering to a infected cells or a patient in need of treatment an effective amount of at least one anti-viral compound, wherein the anti-viral compound comprises a compound having disulfonamide scaffold represented by the following formula (3):

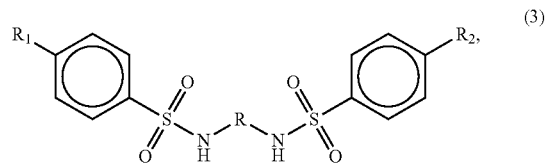

(3)

wherein, independent of each other,
$R_1$ represents an alkyl group,
$R_2$ represents an alkyl group, and
R represents an alkylene group.
Independent of each other includes as to each of $R_1$ and $R_2$.

In another of its aspects, a method for treating retroviral infections and more specifically inhibition of HIV infection comprises administering to an infected cell(s) or a patient in need of treatment an effective amount of at least one anti-viral compound, wherein the anti-viral compound comprises a compound having a disulfonamide scaffold that is represented by the formula (3) in which $R_1$ and $R_2$ are both independently lower alkyl, such as $C_1$-$C_6$ alkyl, and R represents a lower alkylene group. For example, the respective aryl rings can be substituted with lower alkyl, such as a para-alkyl group such as a methyl group, and R represents $-(CH_2)_n-$ in which n is 1-7. An illustrative compound is represented by formula (4):

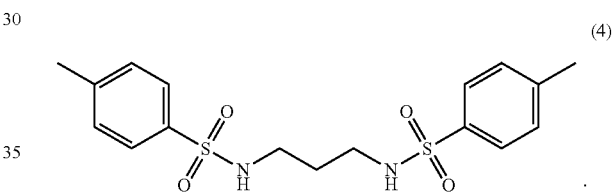

(4)

In another of its aspects, a method for treating retroviral infections and more specifically inhibition of HIV infection comprises administering to an infected cell(s) or a patient in need of treatment an effective amount of at least one anti-viral compound, wherein the anti-viral compound comprises a compound having disulfonamide scaffold represented by the formula (1) in which one of X and Y is lower alkyl, such as $C_1$-$C_6$ alkyl, and R represents a lower alkylene group. For example, in formula (1) an aryl ring can be substituted with lower alkyl, such a para-alkyl group, the other aryl ring can be substituted with a different substituent, such as halogeno, amino, substituted amino, a different alkyl, or alkoxy as examples, and R can represent alkylene, such as lower alkylene $-(CH_2)_n-$ in which n is 1-7. An illustrative compound is represented by formula (5):

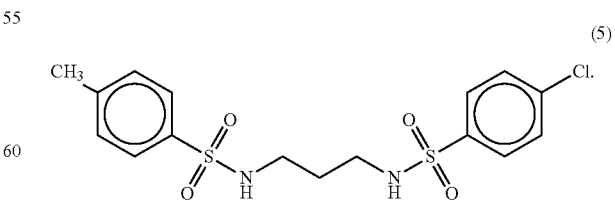

(5)

In another aspect, a method for treating retroviral infections and more specifically inhibition of HIV infection comprises administering to an infected cell(s) or a human or mammal in need of treatment an effective amount of at least one anti-viral compound, in which at least one of the anti-viral compounds is 4-methyl-N-[3-(4-methylbenzenesulfonamido) propyl] benzene sulfonamide ("535").

In another aspect, a method for inhibiting HIV-1 integrase in a cell(s) or in a patient comprises administering to a infected cell(s) or a patient in need of a treatment an effective amount of at least one HIV-1 integrase inhibitor comprising as least one compound represented by any of formulas herein.

In another embodiment, the methods described can be administered as a single or combination therapy with one or more antiretroviral agents for the treatment of retroviral infections including but not limited to HIV infection in humans and mammals. Combination therapy can also include gene therapy.

In another embodiment, a pharmaceutical composition for treating retroviral infections (and inhibiting HIV-1 integrase) comprises at least one compound represented by any of formulas herein as an active ingredient. The pharmaceutical composition will include additional ingredient(s), such as adjuvant(s), as described elsewhere herein.

The compounds represented by the formulas herein may exist in tautomeric or resonance forms. All the tautomeric, resonance and isomeric forms are within the scope of the inventions herein.

The compounds represented by formulas herein can be in a pharmaceutically effective salt or, in principle, other pharmaceutically acceptable forms, such as an ester, and the methods described herein can be practiced with the salt form or such other forms such compound(s). Pharmaceutical forms include those formed, as the case may be, with acetic acid, hydrobromic acid, acetic acid, trifluoroacetic acid, citric acid, oxalic acid, benzoic acid, benzenesulfonic acid, toluenesulfonic acid, sulfuric acid, tartaric acid, fumaric acid, maleic acid, malic acid, lactic acid, and methanesulfonic acid, as examples, although this list is not intended to be limiting insofar as this description is concerned.

The compound(s) and/or their other pharmaceutically acceptable forms (salts as an example) can be administered orally in solid dosage forms, such as capsules, tablets and powders, or in liquid dosage forms, such as elixirs, syrups and suspensions, or injectable forms. It will be appreciated that administration to a cell(s) infected with HIV may be by a different route than administration to a patient. In principle, specialized electrostatic spray apparatus may be used.

It will be appreciated, that a method as described herein can further comprise identifying and selecting a suitable compound, such as a compound represented by formula (1), by conducting a suitable assay(s), such as an HIV-1 assay and/or an integrase assay, and thereafter administering the identified and selected compound to infected cells or to a patient in need of treatment.

It should be understood that the method of using compounds according to any of the formulas herein to treat HIV-1 or to inhibit HIV integrase are novel.

A small molecule inhibitor herein includes a compound represented by a formula herein that binds sites targeting residues of HIV integrase (sometimes referred to as IN or integrase herein) to inhibit HIV integrase (IN). Such compounds within a formula herein include those that bind to a site for at least one of the residues I209, Pro238, Gla221, ASN222, ARG224, LYS240, ASP253, ASN254, K236, K240, K244, R262, R263, LYS266, ILE267, ARG269, and K266, preferably at least two of such residues.

In the above regards, although the CTD is less conserved than that of the NTD and CCD in IN, mutagenesis experiments have identified specific regions in the CTD that are highly conserved. Although CCD on its own can carry out reversal of DNA-strand transfer reaction in vitro, without the NTD and CTD catalysis of 3' processing and strand transfer is impossible.

Mutations made in and around this region, which include residues K236/K240 and R262/R263/K266, resulted in loss of integrase activity and inhibited HIV replication as result of delocalization of IN outside the nucleus of cells.[24-26] It is postulated that one of two things are happening, possibly a significant conformational change upon double or ripple mutations disrupts the SH3 like fold resulting in loss of interaction by nuclear transport receptors and viral proteins necessary for successful integration of vDNA. On the other hand, it is also possible the structural change could also result in loss of IN-DNA binding directly. However, until the present inventions, there has been no prior discovery of a small molecule(s) that binds to such residues (regions) of IN. Therefore, a compound(s) that binds two allosteric sites on the CTD or integrase, one of which has not been previously reported in the literature, and the methods for administering such compound(s) as disclosed herein are novel.

Accordingly, in another aspect, a method for treating against HIV-1 comprises administering a small molecule inhibitor that binds allosteric sites targeting residues K236/K240 and R262/R263/K266 of the C-terminal domain of HIV integrase, with the administering being to target cells or to a patient in need of treatment. A small molecule inhibitor herein includes a compound represented by a formula herein that binds allosteric sites targeting residues K236/K240 and R262/R263/K266 of the C-terminal domain of HIV integrase. Representative compounds include compound 535.

In still another aspect, a method for treating against HIV-1 comprises administering a small molecule inhibitor that binds sites (targeting) at least one of residues ARG262, ARG263, ARG266, LYS244, ILE267, and LYS266 of HIV integrase, with the administering being to target cells or to a patient in need of treatment. The binding with LYS266 may depend on the binding orientation. A small molecule inhibitor herein includes a compound represented by a formula herein that binds sites targeting such residue(s) of HIV integrase, preferably at least two of such residues.

It will therefore be appreciated a compound represented by any of the formulas herein can have an aryl ring may be bonded to the disulfonamide scaffold via an alkyl group, straight or branched. The alkyl group includes a lower alkyl, such as an alkyl group containing 1 to 6 carbon atoms.

In another aspect, a method for treating against HIV-1 comprises administering a small molecule inhibitor that binds sites (targeting) at least one of residues ARG262, ARG263 and ILE267 of HIV integrase, preferably at least two of the residues, with the administering being to target cells or to a patient in need of treatment. A small molecule inhibitor herein includes a compound represented by a formula herein that binds sites targeting such residue(s) of HIV integrase, preferably at least two of such residues.

In a further aspect, a compounds that is novel and within the scope of the formulas herein forms part of the present inventions. The ability to include any provisos deemed appropriate to exclude any compound(s) for any reason from any claim, such as a claim limited to the compounds per se, or from any formula is expressly reserved. Thus, for example, while the complete disclosures of the structure report known as Ali Sheikh et al, Acta Cryst., E67, o1737 (2011), including the references cited therein, the structure report known as Ashfaq et la., Acta. Cryst. E65 01180 (2009), including the references cited therein, and Alyar et al., J. Enzyme Inhibition and Medicinal Chemistry, 2009, 24(4):986-992, including references cited therein, are incorporated herein by reference, an exemplary provisio could exclude the benzene sulfonamides depicted in said structure reports in from a claim to the compounds per se, which is the meaning to be ascribed to the expression "A novel compound having a disulfonamide scaffold selected from those represented by formula . . . ". Thus, exemplary specific provisos subsumed within the foregoing proviso directed to a claim to a compound per se may be X and Y are not both para-methyl substitutents when R is —(CH$_2$)$_3$—, and X and Y are not both hydrogen when R is di-valent C$_3$ or C$_4$ alkylene.

In any of the formulas it will be appreciated that X and/or Y can be hydrocarbyl, but neither is limited thereto. For instance, as disclosed herein, in another of its aspects, in the formulas, X and/or Y, independently of the other, can be halogen (sometimes referred to as halogeno), which includes, for example, bromo, chloro, fluoro, and iodo. It will be appreciated that X and/or Y includes the case when at least one of them (e.g., R$_1$ and R$_2$) is independently alkyl, including lower alkyl, or alkenyl, including lower alkenyl. R$_1$ and R$_2$ can be different or identical. R$_1$ and R$_2$ can, independent of the other, be C$_1$-C$_6$ alkyl. Alkyl includes straight or branched alkyl. When R$_1$ and R$_2$ independently represent a C$_1$-C$_6$ alkyl, exemplary alkyls include aliphatic and branched alkyls, such as methyl, ethyl, propyl, isopropyl, butyl, iso-butyl, pentyl and hexyl, as examples. R$_1$ and/or R$_2$ can be cycloalkyl with 3-6 carbon atoms in the cyclic portion, such as cyclopropyl, cyclopentyl and cyclohexyl, to mention examples. At least one of R$_1$ and R$_2$ can be C$_2$-C$_6$ alkenyl. For example, one of R$_1$ and R$_2$ can be C$_2$-C$_6$ alkenyl and the other can be alkyl.

An X and/or Y substituent can be an amino group (—NH$_2$) or and a substituted amino group (—NR$_3$R$_4$, when R$_3$ and R$_4$ are not both hydrogen). R$_3$ and R$_4$ independently can be alkyl, including lower alkyl, or alkenyl, including lower alkenyl. R$_3$ and R$_4$ can be different or identical. For instance, one of R$_3$ and R$_4$ can be alkenyl, such as a C$_2$-C$_6$ alkenyl, and the other can be alkyl. Each of R$_3$ and R$_4$ can be, independent of the other, a C$_1$-C$_6$ alkyl. Alkyl includes straight or branched alkyl. When R$_3$ and R$_4$ independently represent a C$_1$-C$_6$ alkyl, exemplary alkyls include aliphatic and branched alkyls, such as methyl, ethyl, propyl, isopropyl, butyl, iso-butyl, pentyl and hexyl, as examples. In principle, R$_3$ and/or R$_4$ can be cycloalkyl with 3-6 carbon atoms in the cyclic portion, such as cyclopropyl, cyclopentyl and cyclohexyl, to mention examples. At least one of R$_1$ and R$_2$ can be a C$_2$-C$_6$ alkenyl. Each of R$_3$ and R$_4$ can be, independent of the other, a C$_2$-C$_6$ alkenyl.

It will be appreciated that X and/or Y includes the case when at least one of them (e.g., R$_1$ and R$_2$) is alkoxy, including lower alkoxy, e.g., —OR$_5$ wherein R$_5$ is alkyl, including lower and cyclic alkyl, as discussed above. By way of example, —OR$_5$ includes methoxy, ethoxy, and propoxy (straight or branched). In the case where n and m are greater than 1, each X and each Y is independently selected so that not every X and every Y is alkoxy.

It will be appreciated that a compound represented by formula (1) includes compounds where (Y)$_m$ represents alkyl (methyl, ethyl etc.), and (X)$_n$ represents a halogeno selected from the group consisting of bromo, chloro, fluoro and iodo. For instance as a non-limiting example, when m is 1, and Y is alkyl, and n is 2, 3 or 4, each X is independently selected from the group consisting of bromo, chloro, fluoro and iodo, with the X substituents at the meta, ortho and/or para positions, with it being understood that a Y can be at the meta, ortho or para position. By way of example, when m is at least one, a Y can be alkyl at the para position, and, when n is 2, X can be halogen at any two positions wherein the halogen atoms are the same or different, such as para-bromo and ortho-chloro by way of example. An exemplary compound is represented by formula (6):

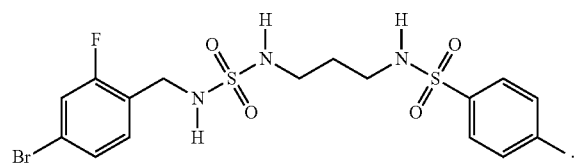 [SMILES: Cc1ccc(S(=O)(=O)NCCCNS(=O)(=O)NCc2ccc(Br)cc2F)cc1]

As mentioned, since X and Y are independently chosen, one can be hydrocarbyl and the other can be another substitutent, such as halogen, alkoxy, amino or a substituted amino, to mention examples. In principle, at least one of X and Y may be hydrogen.

In any of the formulas herein, such as any of formulas (1) through (8), it will be appreciated that R can be a suitable di-valent aryl or alkylene group. For instance, when R is alkylene, it can be lower alkylene. R can be an alkylene group having from one to seven carbon atoms. R is by present preference an alkylene group. An alkylene group includes an aliphatic group, including —(CH$_2$)$_n$— with n being an integer of 1, 2, 3, 4, 5, 6 or 7, e.g., —(CH$_2$)$_3$— by way of example of an R group, but the methods and compounds are not necessarily so limited. When R is di-valent alkylene or di-valent aryl it may or may not be substituted. R can be aryl, such as phenylene as an example.

In one of its aspects, the invention herein relates to the use of at least one compound as described herein as an active ingredient in a pharmaceutical composition, drug or medicament. Accordingly, a compound described is useful in making a drug for treating and/or the prevention of an HIV infection, and/or for reducing HIV replication, and/or for inhibiting HIV integrase (IN), and thus the methods described herein encompass the administration of such a product (drug etc.). A composition with such a compound(s) can include pharmaceutically acceptable carrier(s), vehicle(s) and diluent(s), which include those described in Gennaro et. al. (eds.), Remington, The Science and Practice of Pharmacy, (20$^{th}$ Edition, 2000). The pharmaceutical composition can be formulated based on the mode of administering.

Administering includes orally, parenterally by inhalation spray, topically, rectally, nasally, buccally, vaginally or via an implanted reservoir. Oral administration or administration by injection may be preferable with some patients. The term "parenteral" as used herein includes subcutaneous, intracutaneous, intravenous, intramuscular, intra-articular, intrasynovial, intrasternal, intrathecal, intralesional and intracranial injection or infusion techniques.

For injection, such as a sterile injectable preparation, a sterile injectable aqueous or oleaginous suspension can be used. Such a suspension may be formulated using suitable pharmaceutically acceptable dispersing or wetting agents and suspending agents. The sterile injectable preparation may also be a sterile injectable solution or suspension in a non-toxic parenterally acceptable diluent or solvent. In addition, sterile, fixed oils are conventionally employed as a solvent or suspending medium. For this purpose, any bland fixed oil may be employed including synthetic mono- or diglycerides. For principle, fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant or a similar alcohol.

Orally administered includes any orally acceptable dosage form including, but not limited to, capsules, tablets, and aqueous suspension and solutions. In the case of tablets for oral use, carriers that are commonly used include lactose and corn starch. Lubricating agents, such as magnesium stearate, are also typically added. For oral administration in a capsule form, useful diluents include lactose and dried corn starch. When aqueous suspensions are administered orally, the active ingredient is combined with emulsifying and suspending agents. If desired, certain sweetening and/or flavoring and/or coloring agents may be added.

Administered in the form of suppositories for rectal administration is possible. These compositions can be prepared by mixing a compound of this invention with a suitable non-irritating excipient which is solid at room temperature but liquid at the rectal temperature and therefore will melt in the rectum to release the active components. Such materials include, but are not limited to, cocoa butter, beeswax, and polyethylene glycols.

Topical administration may be useful when the desired treatment involves areas or organs readily accessible by topical application. For application topically to the skin, a composition should be formulated with a suitable ointment containing the active components suspended or dissolved in a carrier. Carriers for topical administration of the compounds of this invention include, but are not limited to mineral oil, liquid petroleum, while petroleum, propylene glycol, polyoxyethylene or polyoxypropylene compound, emulsifying wax and water. Alternatively, compositions can be formulated with a suitable lotion or cream containing the active compound suspended or dissolved in a carrier. Suitable carriers include, but are not limited to, mineral oil, sorbitan monostearate, polysorbate 60, 2-octyldodecanol, benzyl alcohol and water. A composition may also be topically applied to the lower intestinal tract by rectal suppository formulation or in a suitable neat formulation. Topically-transdermal patches are also possible.

Administrating by nasal aerosol or inhalation is another aspect. Such compositions are prepared according to techniques well-known in the art of pharmaceutical formulation and may be prepared as solutions in saline employing benzyl alcohol or other suitable preservatives, absorption promoters to enhance bioavailability, fluorocarbons, and/or other solubilizing or dispersing is another aspect agents known in the art.

In principle, dosage levels of between about 0.01 and about 25 mg/kg body weight per day, preferably between about 0.5 and about 25 mg/kg body weight per day of the active ingredient compound are useful in the prevention and treatment of viral infection, including HIV infection. Typically, the compound (or a pharmaceutical composition) will be administered from about 1 to about 5 times per day or alternatively, as a continuous infusion. Such administration can be used as a chronic or acute therapy. The amount of active ingredient that may be combined with the carrier materials to produce a single dosage form will vary depending upon the patient treated and the particular mode of administration. A typical preparation will contain from about 5% to about 95% active compound (w/w).

As used herein patient in need of treatment refers to a mammal (e.g., a human).

Compounds according to the formulas herein can be prepared by analogy to a synthesis of certain sulfonamides under dynamic pH control in aqueous media. In such a synthesis equimolar amounts of amino compounds and arylsulfonyl chlorides can be employed, and while an organic base could, if desired be used, it may be omitted. In principle, isolation of products involves only filtration after acidification. Excellent yields and purity can be obtained. General synthesis may not entail a work up and further purification. It will be appreciated, however, that work up, purification of the intended compound and verification that the purified compound is the target compound would be appropriate for pharmaceutical applications. The synthesis of compounds of interest can be adapted from Deng et al., Green Chemistry, 8:835-838 (2006); Linden & Bienz, Acta Cryst., C55, IUC9900046 (1999), and Wrede et al., Z. Physiol. Chem., 163:219-228 (1927), the complete disclosures of which are incorporated herein by reference.

The following reaction scheme is presented to exemplify aspects of a suitable synthesis with respect to an illustrative compound (last compound) represented by formula (7):

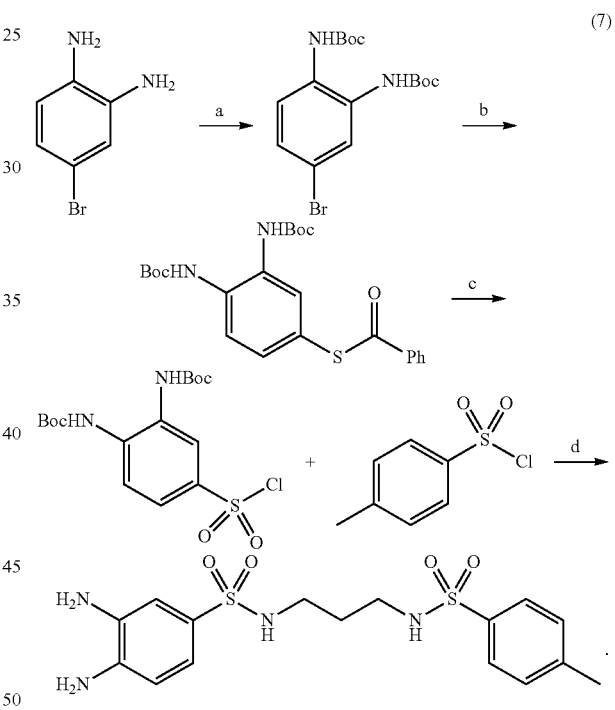

In the above synthesis of a compound represented by formula (7), (a) designates a reaction step with (Boc)$_2$O, 3-methylimidazolium, neat, conducted at room temperature (e.g., 20-25° C.); (b) designates a reaction step with thiobenzoic acid, CuI, i-Pr$_2$Net, in toluene, under reflux conditions for sufficient time for the reaction (e.g., 16 hours lab scale); (c) designates a reaction step with trichloroisocyanuric acid (TCCA), benzyltrimethylammonium chloride (BnMe$_3$NCl), Na$_2$CO$_3$, MeCN, for a suitable time (which may be a relatively short period of time of about 20 min) at about 0° C.; and (d) designates a reaction with 1,3-diaminopropane, in THF, at room temperature (e.g., 20-25° C.) for sufficient time for the reaction (such as about 24 hours lab scale).

Additional compounds can be synthesized by selecting appropriate starting materials. For instance a compound of formula (1) in which (X) is an alkyl group ((X)$_n$ where n=1) and one Y represents an amino and another Y represents a substituted amino group ((Y)$_m$ where Y is NR$_3$R$_4$, where R$_3$ and R$_4$ are alkyl etc., and m=2) includes a compound represented by the formula (8):

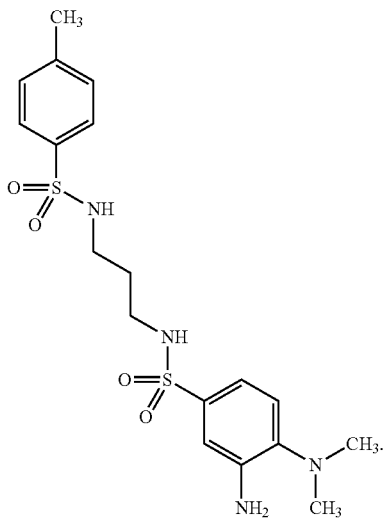 [SMILES: Cc1ccc(S(=O)(=O)NCCCNS(=O)(=O)c2ccc(N(C)C)c(N)c2)cc1]

This sub-class of compounds can be synthesized by using a suitable secondary amine starting material, such as a (2-amino-4-bromophenyl)dialkylamine, e.g., 2-amino-4-bromophenyl)dimethylamine for synthesis of the illustrative species in the formula (7) above. It will be appreciated that other compounds are synthesized by selection of a (2-amino-4-bromophenyl)dialkylamine. For instance the di-alkylamine moiety can be a di-C$_1$-C$_7$ alkylamine, with exemplary alkyls being methyl, ethyl, propyl, isopropyl, butyl, isobutyl, pentyl, hexyl, and heptyl as examples. Thus, (2-amino-4-bromophenyl)diethylamine or (2-amino-4-bromophenyl)dipropylamine, by way of examples, could be selected as a starting material. In principle, each alkyl need not be the same. Thus, a mixed substituted amine moiety is obtainable by selecting a mixed amine, e.g., (2-amino-4-bromophenyl)(alkyl)$_2$amine, of which (2-amino-4-bromophenyl)ethylpropylamine is illustrative.

It will be appreciated that synthesis of other analogs is achievable by selecting the suitable starting materials and reactants. For example, in step (c) in the illustrative reaction scheme a reactant having a substituent other than methyl can be chosen. Similarly, a differently substituted starting material in step (a) can be chosen.

In view of the illustrative synthesis scheme, it will be appreciated that in formula (1) the R group can be selected by appropriate choice of the diamino compound used in a synthesis. Besides 1,3-diaminopropane, other diamino compounds can be selected. For example, other suitable diaminoalkyl compounds include diamino(loweralkyl) compounds, such as 1,4-diaminobutane, 1,5-diaminopentane, 1,6-diaminohexane, 1,7-diaminoheptane and the like. In principle, the diaminoalkyl compound may be cyclic, such as 1,4-diaminocyclohexane. In principle, a diaminoaryl compound, such as 1,4-diaminobenzene or a 1,4-diaminoalkyl-benzene, can be used. By preference the amino groups are terminal groups on the alkyl moieties, which may be the same or different in the case of a diaminoalkylaryl compound.

In assessing a compound according to any of the formulas herein, an assay(s) can be conducted.

An HIV-1 assay can be (is) conducted. A present compound(s) and control compound(s) to be tested are obtained (made or have made). For instance, azidothymidine (AZT) a nucleoside reverse transcriptase inhibitor (NRTI) from Sigma Aldrich. Cell lines can be provided. For example, the Human embryonic kidney 293T cell (Hek293) and HeLa cell line were provided by Dr. Tshaka Cunningham. Mutagenized integrase encoding a fusion protein of enhanced green fluorescent protein with maltose binding protein (eGFP-MBP-IN-R262/3/6A and eGFP-MBP-IN-K236/240) as well as integrase wild type (eGFP-MBP-IN-WT) DNA plasmid and HIV-11entiviral vector encoding eGFP are obtained. In the present case, these were provided by Dr. Mark A. Museing (Rockefeller University).[25] All cell lines were maintained in RPMI 1640 medium supplemented with 10% fetal bovine serum and 1% penicillin and streptomycin. A compound represented by formula (1), (2), (3), (4) or (5) that passes the HIV-1 assay is selected.

In assessing suitability of a compound according to any of the formulas herein, an integrase screening assay can be conducted. In the present case, an exemplary such assay is a cellular integrase assay. A cellular integrase assay can be performed in a 24 well plate. The assay is designed to test compounds in 3-fold serial dilutions (10, 3.3, 1.1 and 0.33 µM) with 0.1% DMSO. Negative and positive control included eGFP-MBP-IN-R262/3/6A, eGFP-MBP-IN-K236/240 and eGFP-MBP-IN-WT respectively supplemented with 0.1% DMSO. Refinement of the assay for optimal results is feasible. For example, refinement herein yields the following protocol. HEK 293T cells (~0.4*10^5 cells/ml) are seeded and incubated at 37° C. (5% CO$_2$) for ~3 days on Poly-L-lysine treated glass coverslips until 80-90% confluent (~3.2*10^5 cells/ml). Next, cells are transfected with 1 µg of eGFP-MBP-INR262/3/6A, eGFP-MBP-IN-K236/240 and eGFP-MBP-IN-WT DNA plasmid simultaneously with test compounds, at varying concentrations mentioned above, using lipofectamine 2000 transfection reagent (µL) at a ratio of 1:2 DNA plasmid to lipofectamine. After 4 hrs of incubation (at 37° C., 5% CO$_2$), the lipofectamine mix is removed and replaced with fresh medium containing serum in the presence of the test compounds. The plate is incubated overnight at 37° C. (5% CO$_2$). Finally cells are treated again with fresh medium containing test compounds and incubated overnight at 37° C. (5% CO$_2$). After a day later (24 hours) cells are fixed with 4% paraformaldehyde in PBS and mounted in DAPI (Vectashield, Vector Laboratories) on glass slides for visualization.[27] The slides are visualized and images, of at least 2 fields per glass disk, are prepared. Images may be prepared using an Olympus 1X51 fluorescence microscope equipped with a camera by way of example. This experiment can be repeated to ensure consistency of results.

In another aspect of assessing suitability of a compound according to any of formulas herein, a HIV-1 lentiviral vector screening assay can be performed. For example, to provide a measure of additional assurance the compounds identified are capable of exhibiting antiviral activity and are capable of permeating into the cells. For example, the HIV-1 lentiviral screening assay can be performed following the HIV assay and/or the integrase assay. For the vector assay HeLa cells can be utilized and the experiment can be performed in a suitable plate, such as a 24 well plate. In a manner similar to the integrase assay, the experiment can be designed to test further the compounds, such as compounds that passed another suitable assay, such as the HIV-1 screening assay or the integrase screening assay, with 2-fold serial dilution (60, 30, 15, 7.5 and 3.7 µM) in parallel with HIV-1 lentiviral vector and controls. A negative control, e.g., AZT, and a positive control as vector only and blank as un-infected are appropriately selected. Again, the concentration of DMSO was limited to 0.1%. Hela cells (~3.2-10^5 cells/ml) were infected with HIV-1 lentiviral vector in the presence of the compounds to be tested and controls. After the first 24 hours of incubation at 37° C. (5% $CO_2$), cells are replaced with fresh media containing test compounds and incubated for an additional 24 hrs. Cells are fixed with 4% paraformaldehyde in PBS and mounted in DAPI on glass slides for visualization and quantification. Images, of at least 2 fields per glass disk are obtained, such as images taken with an Olympus 1X51 fluorescence microscope equipped with a camera. EGFP fluorescence spanning an average area of 12*10^5 square pixels is quantified using Image J software, from which $IC_{50}$ values can bee extrapolated using graph pad PRISM software.

It will be appreciated that in vitro testing, which may include the screening(s) described above, would be indicative of efficacy in a method of treating a patient or treating cells as described herein. Allosteric inhibitory activities are confirmed by the assay(s).

It will be appreciated that use of a compound herein for a method as described is unrelated to any method of treatment for a microbial infection. In other words, antiviral activity would be unexpected even if a compound may exhibit antimicrobial activity. A patient population herein constitutes patients in need of treatment against HIV, which includes a method for inhibition of HIV integrase.

Therefore in another of its aspects, as discussed above, the discovery includes any of the methods disclosed and further comprises providing a compound within the scope of the formulas is one that assayed as exhibiting antiviral activity (anti-HIV 1; inhibitor of IN), and using the compound in the method of treatment or the method of inhibiting IN as described herein, particularly for the preferred patient population.

The amino acid sequence for IN is described in Crystal structure of the HIV-1 integrase catalytic core and C-terminal domains: a model for viral DNA binding, Proc. Natl. Acad. Sci., USA 97:8233-8238.

EXAMPLES

The following non-limiting example(s) further describe(s) aspects of the present inventions.

In conducting the HIV assay, a representative test compound was obtained (TimTec) and azidothymidine (AZT) a nucleoside reverse transcriptase inhibitor (NRTI) were obtained from Sigma Aldrich. A Human embryonic kidney 293T cell (Hek293) and a HeLa cell line were obtained from Dr. Tshaka Cunningham. Mutagenized integrase encoding a fusion protein of enhanced green fluorescent protein with maltose binding protein (eGFP-MBP-IN-R262/3/6A and eGFP-MBP-IN-K236/240) as well as integrase wild type (eGFP-MBP-IN-WT) DNA plasmid and HIV-1 lentiviral vector encoding eGFP were obtained from Dr. Mark A. Museing (Rockefeller University). All cell lines were maintained in RPMI 1640 medium supplemented with 10% fetal bovine serum and 1% penicillin and streptomycin.

As an integrase screening assay, a cellular integrase assay was performed in a 24 well plate. The experiment was designed to test all compounds in 3-fold serial dilutions (10, 3.3, 1.1 and 0.33 µM) with 0.1% DMSO. Negative and positive control included eGFP-MBP-IN-R 262/3/6A, eGFP-MBP-IN-K236/240 and eGFP-MBP-IN-WT respectively supplemented with 0.1% DMSO. Optimization of the assay resulted in the following protocol. HEK 293T cells (~0.4*10^5 cells/ml) were seeded and incubated at 37° C. (5% $CO_2$) for ~3 days on Poly-L-lysine treated glass coverslips until 80-90% confluent (~3.2*10^5 cells/ml). Next, cells were transfected with 1 µg of eGFP-MBP-INR262/3/6A, eGFP-MBP-IN-K236/240 and eGFP-MBP-IN-WT DNA plasmid simultaneously with test compounds, at varying concentrations mentioned above, using lipofectamine 2000 transfection reagent (µL) at a ratio of 1:2 DNA plasmid to lipofectamine. After 4 hrs of incubation (@ 37° C., 5% $CO_2$), the lipofectamine mix was removed and replaced with fresh medium containing serum in the presence of the test compounds. Plate was incubated overnight at 37° C. (5% $CO_2$). Finally cells were treated again with fresh medium containing test compounds and incubated overnight at 37° C. (5% $CO_2$). 24 hours later cells were fixed with 4% paraformaldehyde in PBS and mounted in DAPI (Vectashield, Vector Laboratories) on glass slides for visualization.[27] Slides were visualized and images, of at least 2 fields per glass disk, were taken with an Olympus 1X51 fluorescence microscope equipped with a camera. This experiment was repeated to ensure consistency of results.

A HIV-1 lentiviral vector screening assay was additionally performed after the integrase assay to help assure that a compound identified and selected exhibited antiviral activity and the capability to adequately permeate cells of interest (cells from or in a patient, such as a patient in need of treatment). For the vector assay HeLa cells were utilized and the HIV-1 lentiviral vector screening was performed in a 24 well plate. In a manner similar to the integrase assay, the HIV-1 lentiviral vector assay tested the compound(s) from the integrase assay, with 2-fold serial dilution (60, 30, 15, 7.5 and 3.7 µM) in parallel with HIV-1 lentiviral vector and controls. As the negative control AZT was used, a positive control as vector only and blank as un-infected were additionally used. Again the concentration of DMSO was limited to 0.1%. Hela cells (~3.2*10^5 cells/ml) were infected with HIV-1 lentiviral vector in the presence of the compound(s) tested and controls. After the first 24 hours of incubation at 37° C. (5% $CO_2$), cells were replaced with fresh media containing test compounds and incubated for an additional 24 hrs. Cells were fixed with 4% paraformaldehyde in PBS and mounted in DAPI on glass slides for visualization and quantification. Images, of at least 2 fields per glass disk were taken with an Olympus 1X51 fluorescence microscope equipped with a camera. EGFP fluorescence spanning an average area of 12*10^5 square pixels was quantified using Image J software, from which $IC_{50}$ values were extrapolated using graph pad PRISM software.

Since the discovery of a potent nuclear localization signal (NLS) located on the C-terminal domain of HIV-1 integrase, mutagenesis experiments have identified amino acid residues 236/240 and 262/263/266 as essential for modulating HIV IN nuclear import.[25] With the aid of structure-based virtual screening equipped with the knowledge of two allosteric sites essential for HIV IN nuclear import, compounds of promise are identified. While not wishing to limit the scope of the present discoveries by a hypothesis, it appears from the present discoveries that small molecules can function as inhibitors by binding to certain amino acid residues in IN so as to block the IN, e.g., inhibit it from functioning. For example, a small molecule within the scope of formula (1), such as compound 535, that binds amino acid residues 236/240 or 262/263/266 will display a nuclear exclusion phenotype like or similar to that of mutant HIV-IN DNA plasmids eGFP-MBP-IN-R262/3/6A and eGFP-MBP-IN-K236/240.

For example, to illustrate the foregoing methodology, a presently preferred compound from amongst those compounds tested, 4-methyl-N-[3-(4-methylbenzenesulfonamido) propyl] benzene sulfonamide ("535"), is representative and it exhibited inhibition sufficient to prevent nuclear import of integrase. This is indicative that a compound having efficacy as determined by the screening disclosed herein would be useful in a method as described herein.

FIG. 1A clearly shows transfected HIV-1 IN accumulates within the nuclei of cells, while transfected NLS mutant integrase, eGFP-MBP-IN-R262/3/6A, was extranuclear with integrase mostly localized within the cytoplasm of cells (FIG. 1B). The representative compound ("535") (FIGS. 1C & 1D) depicted similar phenotypic results as that of eGFP-MBP-IN-R262/3/6A, which clearly demonstrates inhibition of nuclear import of IN. In FIGS. 1C and 1D, for cells expressing eGFP-IN, fluorescence is observed in the cytoplasmic region, confirmed by the DAPI staining of the nucleus (blue images) which is the obvious dark vacuoles in the GFP images.

The validation of the compound(s) as an inhibitor of HIV-1 IN nuclear import via a representative compound was seen in subsequent experimental validation of its effectiveness as an antiretroviral (ARV) and its ability to permeate the cells.

Figure 2:
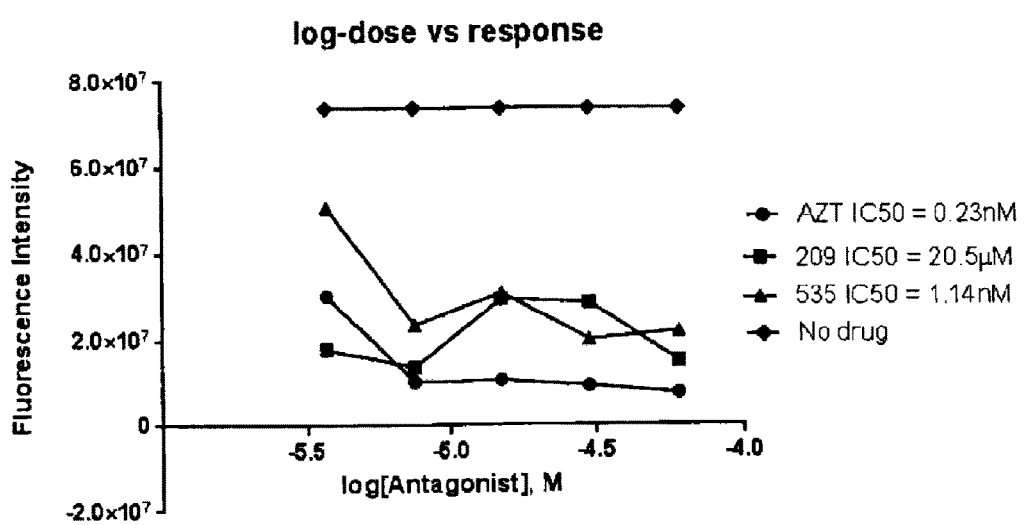
FIG. 2 is a dose response curve of an exemplary test compound and AZT.

The advantage of IN screening assay is the plasma membrane of the cells was permeabilized using lipofectamine which perforates the cell membrane without compromising the integrity of the cell. As a result easy transport and deposition of both drug and fluorescent IN across the cell membrane into the cytoplasm is achieved. Lentiviral vector assay on the other hand does not involve transfection therefore allows for passive transport of test inhibitors across the cell membrane. HIV-1 lentiviral vector screening of the representative compound and its combination of with AZT as the negative control was conducted. AZT exhibited remarkable antiviral activity in cell culture (IC50 0.23 nM) as expected. In comparison, the representative compound (IC50 1.14 nM) exhibited micromolar and nanomolar activity respectively (FIG. 2).

FIG. 1 depicts the C-terminal domain of HIV-1 IN, nuclear import inhibition screening assay results. (HEK 293T cells transfected with HIV-1 integrase (C-terminal domain) DNA plasmid encoding enhanced green fluorescent fusion protein and maltose binding protein (eGFPMBP IN).)

In FIG. 1(A) the positive control, eGFP-MBP-IN-WT with no drug results in nuclear localization of IN is shown.

In FIG. 1(B) the negative control, eGFP-MBP-IN-R262/3/6A chimeric triple mutant exhibiting nuclear exclusion of the fusion protein is shown.

In FIG. 1(C) another test compound ("209") with eGFP-MBP-IN-WT exhibiting similar phenotype as that of eGFP-MBP-IN-R262/3/6A that is, nuclear exclusion of the fusion protein.

In FIG. 1(D) shows the representative test compound ("535") with eGFP-MBP-IN-WT exhibiting again nuclear exclusion of the fusion protein in majority of cells.

FIG. 2 graphically presents the dose response curves of a representative compound ("535") and AZT. A HIV-1 lentiviral vector cell culture screening assay protocol was applied for testing antiviral activity of the test compounds. When comparing the effect of the representative test compound and the negative control AZT to HIV infectivity in the presence of no drug (Fluorescence Intensity $7.0*10^7$), all the test compounds exhibited an inhibitory effect in a dose dependent manor Integration of HIV-1 viral genome into host DNA, located in the nucleus of cells, is an essential step for HIV infection. Nuclear import of integrase is impossible without the formation of pre-integration complex (PIC) which is recognized by members of the importin family and nuclear pore protein which transports PIC complex to the nucleus where integration occurs.[5,28] With a complete understanding of the mechanism of action of IN and the evolution of N resistant mutations is still unfolding, it is postulated that IN may represent a target for new ARV drugs.

Novel integrase inhibitors have been discovered as described herein that bind to sites in IN to inhibit its activity such inhibitors include compounds that bind allosteric sites on the C-terminal domain of the protein.

Advantageously, there is no human homolog of IN enzyme, hence disrupting the function of IN should be tolerable, if not harmful, to human physiology. Therefore, a significant unexpected attribute of the present inventions lies in targeting residues that are less susceptible to mutation and are essential for integrase activity.

Advantageously, useful application of a present active ingredient that targets these regions according to a present method, which can contribute to lower HIV infection rates and increasing life expectancy of a patient.

Present indications are that HIV patients may be less likely develop resistance to the drug.

The results of the integrase screening assay clearly showed the representative compound displayed inhibition of nuclear import of IN similar to that of the triple mutant chimeric IN. However, further work showed this result translates to inhibition of HIV replication in cells from the standpoints of drug permeability and selectivity. For instance, results of the lentiviral vector screening indicate, without optimization, the representative compound clearly inhibited HIV-1 replication in a dose-dependent manor and at high concentrations without introducing cellular toxicity.

The complete disclosure of all the references cited herein is incorporated herein by reference.
1. UNAIDS UNAIDS report on the global AIDS epidemic.; Joint United Nations Programme on HIV/AIDS (UNAIDS): 12.
2. Menendez-Arias, L. Molecular basis of human immunodeficiency virus type 1 drug resistance: overview and recent developments. Antiviral Res. 2013, 98 (1), 93-120.
3. Archin, N. M.; Liberty, A. L.; Kashuba, A. D.; Choudhary, S. K.; Kuruc, J. D.; Crooks, A. M.; Parker, D. C.; Anderson, E. M.; Kearney, M. F.; Strain, M. C.; Richman, D. D.; Hudgens, M. G.; Bosch, R. J.; Coffin, J. M.; Eron, J. J.; Hazuda, D. J.; Margolis, D. M. Administration of vorinostat disrupts HIV-1 latency in patients on antiretroviral therapy. Nature 2012, 487 (7408), 482-485.
4. Archin, N. M.; Keedy, K. S.; Espeseth, A.; Dang, H.; Hazuda, D. J.; Margolis, D. M. Expression of latent human immunodeficiency type 1 is induced by novel and selective histone deacetylase inhibitors. AIDS 2009, 23 (14), 1799-1806.
5. Zhan, P.; Liu, X.; De, C. E. Blocking nuclear import of pre-integration complex: an emerging anti-HIV-1 drug discovery paradigm. Curr. Med. Chem. 2010, 17 (6), 495-503.
6. Brown, P. O. Integration; Outline of the Integration process. In Retroviruses, Coffin J M, Hughes S H, Varmus H E ed.; Cold Spring Harbor Laboratory Press: 1997.

7. Whittaker, G. R.; Kann, M.; Helenius, A. Viral entry into the nucleus. Annu. Rev. Cell Dev. Biol. 2000, 16, 627-651.
8. Ceccherini-Silberstein, F.; Malet, I.; D'Arrigo, R.; Antinori, A.; Marcelin, A. G.; Perno, C. F. Characterization and structural analysis of HIV-1 integrase conservation. AIDS Rev. 2009, 11(1), 17-29.
9. Quashie, P. K.; Mesplede, T.; Wainberg, M. A. Evolution of HIV integrase resistance mutations. Curr. Opin. Infect. Dis. 2013, 26 (1), 43-49.
10. FDA, FDA approval of Isentress (raltegravir). U.S. Food and Drug Administration (FDA). Jun. 25, 2009.
11. FDA, Approval of new fixed dose combination, Stribild (elvitegravir, cobicistat, emtricitabine, tenofovir disoproxil fumarate). U.S. Food and Drug Administration. Nov. 7, 2012.
12. Olin, J. L.; Spooner, L. M.; Klibanov, O. M. Elvitegravir/cobicistat/emtricitabine/tenofovir disoproxil fumarate single tablet for HIV-1 infection treatment. Ann. Pharmacother. 2012, 46 (12), 1671-1677.
13. Gilead, Gilead Receives Complete Response Letters from U.S. Food and Drug Administration for Elvitegravir and Cobicistat. Gilead Sciences, Inc., Apr. 30, 2013. Gilead.
14. Malet, I.; Delelis, O.; Valantin, M. A.; Montes, B.; Soulie, C.; Wirden, M.; Tchertanov, L.; Peytavin, G.; Reynes, J.; Mouscadet, J. F.; Katlama, C.; Calvez, V.; Marcelin, A. G., Mutations associated with failure of raltegravir treatment affect integrase sensitivity to the inhibitor in vitro. Antimicrob. Agents Chemother. 2008, 52 (4), 1351-1358.
15. Shimura, K.; Kodama, E.; Sakagami, Y.; Matsuzaki, Y.; Watanabe, W.; Yamataka, K.; Watanabe, Y.; Ohata, Y.; Doi, S.; Sato, M.; Kano, M.; Ikeda, S.; Matsuoka, M., Broad antiretroviral activity and resistance profile of the novel human immunodeficiency virus integrase inhibitor elvitegravir (JTK-303/GS-9137). 1 Virol. 2008, 82 (2), 764-774.
16. Malet, I.; Calvez, V.; Marcelin, A. G., The future of integrase inhibitors of HIV-1. Curr. Opin. Virol. 2012, 2 (5), 580-587.
17. Christ, F.; Voet, A.; Marchand, A.; Nicolet, S.; Desimmie, B. A.; Marchand, D.; Bardiot, D.; Van der Veken, N. J.; Van, R. B.; Strelkov, S. V.; De, M. M.; Chaltin, P.; Debyser, Z. Rational design of small-molecule inhibitors of the LEDGF/p75-integrase interaction and HIV replication. Nat. Chem. Biol. 2010, 6 (6), 442-448.
18. Christ, F.; Shaw, S.; Demeulemeester, J.; Desimmie, B. A.; Marchand, A.; Butler, S.; Smets, W.; Chaltin, P.; Westby, M.; Debyser, Z.; Pickford, C. Small-molecule inhibitors of the LEDGF/p75 binding site of integrase block HIV replication and modulate integrase multimerization. Antimicrob. Agents Chemother. 2012, 56 (8), 4365-4374.
19. Wang, J. Y.; Ling, H.; Yang, W.; Craigie, R. Structure of a two-domain fragment of HIV-1 integrase: implications for domain organization in the intact protein. EMBO J., 2001, 20 (24), 7333-7343.
20. Chen, J. C.; Krucinski, J.; Miercke, L. J.; Finer-Moore, J. S.; Tang, A. H.; Leavitt, A. D.; Stroud, R. M. Crystal structure of the HIV-1 integrase catalytic core and C-terminal domains: a model for viral DNA binding. Proc. Natl. Acad. Sci. U S A 2000, 97 (15), 8233-8238.
21. McColl, D. J.; Chen, X., Strand transfer inhibitors of HIV-1 integrase: bringing IN a new era of antiretroviral therapy. Antiviral Res. 2010, 85 (1), 101-118.
22. Zheng, R.; Jenkins, T. M.; Craigie, R., Zinc folds the N-terminal domain of HIV-1 integrase, promotes multimerization, and enhances catalytic activity. Proc. Natl. Acad. Sci. U S. A 1996, 93 (24), 13659-13664.
23. Engelman, A.; Craigie, R., Identification of conserved amino acid residues critical for human immunodeficiency virus type 1 integrase function in vitro. J. Virol. 1992, 66 (11), 6361-6369.
24. Lu, R.; Ghory, H. Z.; Engelman, A., Genetic analyses of conserved residues in the carboxyl-terminal domain of human immunodeficiency virus type 1 integrase. J. Virol. 2005, 79 (16), 10356-10368.
25. Muesing, M. A.; Cunningham, T. J., Nuclear localization signal of lentiviral integrase and methods of use thereof. US 20060134651A1, Jun. 22, 2006.
26. Wiskerchen, M.; Muesing, M. A. Human immunodeficiency virus type 1 integrase: effects of mutations on viral ability to integrate, direct viral gene expression from unintegrated viral DNA templates, and sustain viral propagation in primary cells. J. Virol. 1995, 69 (1), 376-386.
27. Mousnier, A.; Leh, H.; Mouscadet, J. F.; Dargemont, C. Nuclear import of HIV-1 integrase is inhibited in vitro by styrylquinoline derivatives. Mol. Pharmacol. 2004, 66 (4), 783-788.
28. Levin, A.; Armon-Omer, A.; Rosenbluh, J.; Melamed-Book, N.; Graessmann, A.; Waigmann, E.; Loyter, A. Inhibition of HIV-1 integrase nuclear import and replication by a peptide bearing integrase putative nuclear localization signal. Retrovirology. 2009, 6, 112.

What is claimed is:

1. A method for inhibiting HIV integrase in target cells or in a patient by targeting an allosteric binding site of HIV integrase comprises administering to said target cells or to said patient in need of treatment an effective amount of at least one anti-viral compound, wherein the anti-viral compound comprises a compound having disulfonamide scaffold represented by the following general formula (1):

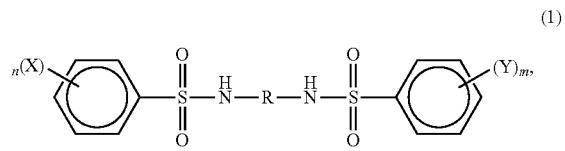

wherein, independent of each other, each X independently represents hydrocarbyl, halogeno, amino, substituted amino, or alkoxy, wherein substituted amino is represented by —NR$_3$,R$_4$ wherein R$_3$ and R$_4$, are not both hydrogen and independently represent alkyl or alkenyl, n is an integer of 0, 1, 2, 3 or 4, each Y independently represents hydrocarbyl, halogeno, amino, substituted amino or alkoxy, wherein substituted amino is represented by —NR$_3$,R$_4$ wherein R$_3$ and R$_4$, are not both hydrogen and independently represent alkyl or alkenyl, wherein both X and Y are not alkoxy, m is an integer of 0, 1, 2, 3 or 4, and R represents di-valent hydrocarbyl, substituted or unsubstituted.

2. A method for inhibiting HIV integrase according to claim 1, wherein X and Y independently represent lower alkyl.

3. A method for inhibiting a HIV integrase according to claim 2, wherein X and Y independently represent C$_1$-C$_6$ alkyl.

4. A method for inhibiting a HIV integrase according to claim 1, wherein one of X and Y is lower alkyl and the other is halogeno, amine or substituted amine.

5. A method for inhibiting HIV integrase according to claim 3, wherein n is 1 and m is 1, X and Y are independent of one another and represent para-substitutents.

6. A method for inhibiting HIV integrase according to claim 5, wherein R represents $C_1$-$C_7$ divalent alkylene group.

7. A method for inhibiting HIV integrase according to claim 1, wherein R represents an alkylene group having one to seven carbon atoms, X and Y are para-substitutents, and one of X and Y is lower alkyl and the other is halogeno.

8. A method for inhibiting HIV integrase according to claim 1, wherein X and Y are independent of one another and represent para-substitutents and R represents an alkylene group having one to seven carbon atoms.

9. A method for inhibiting HIV integrase according to claim 5, wherein R represents —$(CH_2)_3$—.

10. A method for inhibiting a HIV integrase according to claim 8, wherein one of X and Y is methyl and the other is chloro.

11. A method for inhibiting a HIV integrase according to claim 7, wherein one X and Y is halogeno and the other is methyl.

12. A method for inhibiting a HIV integrase according to claim 1, wherein at least one of X and Y is amine.

13. A method for inhibiting a HIV integrase according to claim 1, wherein when n is 1 and m is 2, one Y is substituted amino and the other Y is amino.

14. A method for inhibiting HIV integrase according to claim 1, wherein R represents an alkylene group having one carbon atom.

15. A method for inhibiting HIV integrase according to claim 14, wherein
one of X and Y is lower alkyl and the other is halogeno, amine or substituted amine;
X and Y independently of the other represent $C_1$-$C_6$ alkyl;
n is 1 and m is 1, and X and Y are independent of one another and represent para-substitutents; or
at least one of X and Y is amine.

16. A method for inhibiting HIV integrase according to claim 14, wherein n is 1 and m is 1 and one of X and Y is lower alkyl and the other is halogen.

17. A method for inhibiting HIV integrase according to claim 1, wherein X is represented by —$NR_3,R_4$ wherein $R_3$ and $R_4$, are not both hydrogen and independently represent alkyl or alkenyl, or Y is represented by —$NR_3,R_4$ wherein $R_3$ and $R_4$, are not both hydrogen and independently represent alkyl or alkenyl, or X and Y, independent of the other, represent —$NR_3,R_4$ wherein $R_3$ and $R_4$, are not both hydrogen and independently represent alkyl or alkenyl.

18. A method for inhibiting HIV integrase in target cells or in a patient according to claim 1, wherein the at least one anti-viral compound comprises a compound represented by the formula:

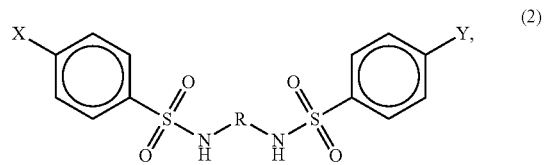

(2)

wherein
X represents a $C_1$-$C_6$ alkyl group selected from the group consisting of methyl, ethyl, propyl, butyl, pentyl, and hexyl;
Y represents a $C_1$-$C_6$ alkyl group selected from the group consisting of methyl, ethyl, propyl, butyl, pentyl, and hexyl; and
R is a divalent —$(CH_2)_n$— alkylene group where n is an integer of 1 to 7.

19. A method for inhibiting HIV integrase in target cells or in a patient according to claim 18, wherein the antiviral compound comprises 4-methyl-N-[3-(4-methylbenzenesulfonamido)propyl]benzene sulfonamide.

20. A method for inhibiting HIV integrase in target cells or in a patient according to claim 18, wherein X is methyl and Y is methyl.

* * * * *